(12) United States Patent
Melkent et al.

(10) Patent No.: US 11,918,482 B2
(45) Date of Patent: Mar. 5, 2024

(54) EXPANDABLE INTERBODY IMPLANT

(71) Applicant: Warsaw Orthopedic, Inc., Warsaw, IN (US)

(72) Inventors: Anthony J. Melkent, Germantown, TN (US); William D. Armstrong, Memphis, TN (US); Stanley T. Palmatier, Olive Branch, MS (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 451 days.

(21) Appl. No.: 17/346,988

(22) Filed: Jun. 14, 2021

(65) Prior Publication Data

US 2021/0298916 A1 Sep. 30, 2021

Related U.S. Application Data

(62) Division of application No. 15/926,493, filed on Mar. 20, 2018, now Pat. No. 11,033,402, which is a
(Continued)

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2002/30428* (2013.01);
(Continued)

(58) Field of Classification Search
CPC ............................................ A61F 2/4455–447
See application file for complete search history.

(56) References Cited

U.S. PATENT DOCUMENTS 6,491,724 B1 12/2002 Ferree
7,828,849 B2 11/2010 Lim
(Continued)

FOREIGN PATENT DOCUMENTS

AU 2014100879 9/2014
CN 203183090 9/2013
(Continued)

OTHER PUBLICATIONS

Examination Report dated Oct. 28, 2017 for Australian Application No. 2015343514.
(Continued)

*Primary Examiner* — Amy R Sipp

(57) ABSTRACT

An expandable interbody implant adapted for insertion at least into a disc space, between two adjacent vertebrae of a spine. An upper member and a lower member are pivotally connected at least by a drive link. A bone graft storage portion packed with a selected volume of bone growth material. A translational wall is provided between the bone graft storage portion and a trailing end of the implant. An actuator engages the bone graft storage portion, pushing it forward into engagement with the drive link, which pivots upward, moving the upper member upward away from the lower member. Upward movement of the upper member raises the translational wall to a position to assist in retention of the selected volume bone graft material within the hollow portion of the bone graft storage portion. Upward rotation of the drive link brings a face thereof into contact with a front of the bone graft storage portion, thereby retaining near constant volume of the bone graft material.

20 Claims, 7 Drawing Sheets

Related U.S. Application Data division of application No. 14/532,636, filed on Nov. 4, 2014, now Pat. No. 9,937,053.

(52) U.S. Cl.
CPC .............. *A61F 2002/30471* (2013.01); *A61F 2002/30507* (2013.01); *A61F 2002/30538* (2013.01); *A61F 2002/30581* (2013.01); *A61F 2002/30593* (2013.01); *A61F 2002/30904* (2013.01)

(56) References Cited

U.S. PATENT DOCUMENTS

| | | | |
|---|---|---|---|
| 7,850,733 | B2 | 12/2010 | Baynham et al. |
| 7,875,078 | B2 | 1/2011 | Wysocki et al. |
| 7,909,869 | B2 | 3/2011 | Gordon et al. |
| 8,062,375 | B2 | 11/2011 | Glerum et al. |
| 8,105,358 | B2 | 1/2012 | Phan |
| 8,105,382 | B2 | 1/2012 | Olmos et al. |
| 8,123,810 | B2 | 2/2012 | Gordon et al. |
| 8,133,232 | B2 | 3/2012 | Levy et al. |
| 8,187,332 | B2 | 5/2012 | McLuen |
| 8,382,842 | B2 | 2/2013 | Greenhalgh et al. |
| 8,394,145 | B2 | 3/2013 | Weiman |
| 8,398,713 | B2 | 3/2013 | Weiman |
| 8,403,990 | B2 | 3/2013 | Dryer et al. |
| 8,435,298 | B2 | 5/2013 | Weiman |
| 8,491,659 | B2 | 7/2013 | Weiman |
| 8,518,120 | B2 | 8/2013 | Glerum et al. |
| 8,523,944 | B2 | 9/2013 | Jimenez et al. |
| 8,556,979 | B2 | 10/2013 | Weiman et al. |
| 8,568,481 | B2 | 10/2013 | Olmos |
| 8,628,577 | B1 | 1/2014 | Jimenez |
| 8,628,578 | B2 | 1/2014 | Miller et al. |
| 8,632,595 | B2 | 1/2014 | Weiman |
| 8,663,329 | B2 | 3/2014 | Ernst |
| 8,679,183 | B2 | 3/2014 | Glerum et al. |
| 8,685,098 | B2 | 4/2014 | Glerum et al. |
| 8,709,086 | B2 | 4/2014 | Glerum et al. |
| 8,778,025 | B2 | 7/2014 | Ragab et al. |
| 8,795,366 | B2 | 8/2014 | Varela |
| 8,888,853 | B2 | 11/2014 | Glerum et al. |
| 8,888,854 | B2 | 11/2014 | Glerum et al. |
| 8,894,711 | B2 | 11/2014 | Varela |
| 8,894,712 | B2 | 11/2014 | Varela |
| 8,926,704 | B2 | 1/2015 | Glerum |
| 8,940,049 | B1 | 1/2015 | Jimenez |
| 9,039,771 | B2 | 5/2015 | Glerum et al. |
| 9,119,730 | B2 | 9/2015 | Glerum et al. |
| 9,801,734 | B1* | 10/2017 | Stein ..................... A61F 2/447 |
| 2002/0068977 | A1 | 6/2002 | Jackson |
| 2002/0128713 | A1 | 9/2002 | Ferree et al. |
| 2006/0206207 | A1 | 9/2006 | Dryer et al. |
| 2011/0054621 | A1 | 3/2011 | Lim |
| 2011/0093074 | A1* | 4/2011 | Glerum .................. A61F 2/447 623/17.16 |
| 2011/0172714 | A1 | 7/2011 | Varela |
| 2011/0172721 | A1 | 7/2011 | Varela |
| 2012/0029636 | A1 | 2/2012 | Ragab et al. |
| 2012/0035729 | A1 | 2/2012 | Glerum et al. |
| 2012/0059470 | A1* | 3/2012 | Weiman .................. A61F 2/442 623/17.11 |
| 2012/0109319 | A1 | 5/2012 | Perisic |
| 2012/0150304 | A1 | 6/2012 | Glerum et al. |
| 2012/0150305 | A1 | 6/2012 | Glerum et al. |
| 2012/0158146 | A1 | 6/2012 | Glerum et al. |
| 2012/0158147 | A1 | 6/2012 | Glerum et al. |
| 2012/0158148 | A1 | 6/2012 | Glerum et al. |
| 2012/0185049 | A1* | 7/2012 | Varela ..................... A61F 2/447 623/17.16 |
| 2013/0144388 | A1 | 6/2013 | Emery et al. |
| 2013/0158664 | A1* | 6/2013 | Palmatier .............. A61F 2/4425 623/17.16 |
| 2013/0190876 | A1* | 7/2013 | Drochner .............. A61F 2/4455 623/17.16 |
| 2013/0197642 | A1* | 8/2013 | Ernst ...................... A61F 2/442 623/17.16 |
| 2014/0121774 | A1 | 5/2014 | Glerum et al. |
| 2014/0249629 | A1* | 9/2014 | Moskowitz ........... A61F 2/4611 623/17.15 |
| 2014/0277500 | A1* | 9/2014 | Logan ..................... A61F 2/447 623/17.16 |
| 2014/0324171 | A1 | 10/2014 | Glerum et al. |
| 2016/0250034 | A1 | 9/2016 | Loebl |

FOREIGN PATENT DOCUMENTS

| | | |
|---|---|---|
| CN | 103830023 | 6/2014 |
| CN | 103876865 | 6/2014 |
| CN | 104023675 | 9/2014 |
| KR | 100905962 | 7/2009 |
| WO | 2015063721 | 5/2015 |

OTHER PUBLICATIONS

Office Action dated Jul. 12, 2018 for Chinese Application No. 201580071502.6.
Office Action (English Translation) dated Jul. 12, 2018 for Chinese Application No. 201580071502.6.
European Search Report dated May 4, 2018 for EP15856782.6.
International Search Report and Written Opinion dated Feb. 2, 2016 for PCT/US2015/056929.
Office Action dated Jul. 20, 2022 for Korean Application No. 10-2017-7013577.

* cited by examiner

EXPANDABLE INTERBODY IMPLANT

The present application is a divisional of U.S. application Ser. No. 15/926,493, filed Mar. 20, 2018; which is a divisional of U.S. application Ser. No. 14/532,636, filed Nov. 4, 2014; all of which is incorporated by reference herein.

BACKGROUND OF THE INVENTION

The present invention relates generally to an expandable interbody implant, and more particularly to a lordotic expandable interbody implant adapted for oblique posterior, oblique anterior, co-axial posterior, or co-axial anterior, insertion and placement in a disc space having a surgically-corrected height between adjacent vertebral bodies in the lumbar spine.

DESCRIPTION OF THE RELATED ART

Lordotic expandable spinal fusion implants are known in the art. The lordotic, tapered configuration of such known implants assists in the restoration or enhancement of spinal lordosis in the lumbar spine. The expandability of such implants allows placement of a potentially larger implant through a smaller opening in a patient's body, with selective expansion in a selected direction providing the advantage of increasing the height of the implant and corresponding distraction of the disc space, without a concomitant increase in the width of the implant. The related art implants, however, have certain disadvantages.

For example, the configurations of the leading ends of the related art implants limit the preferred placement of the implants in the disc space to be along an axis defined between the anterior and posterior portion of the disc space. Oblique placement has not been optimized with the related art implants.

The related art implants, moreover, typically employ ramp-on-ramp linkage mechanisms, which have proven to be unreliable in enabling such implants to smoothly and reliably increase to a selected height desired by the surgeon.

In addition, the related art implants have experienced difficulty with maintaining, during insertion and expansion within the disc space, a selected volume of bone graft material stored in the implant. During expansion of such related-art implants within the disc space, some of the stored bone graft material often escapes, thereby reducing the selected volume of bone graft material stored in the implant.

SUMMARY OF THE INVENTION

It is an object of the present invention to provide an expandable interbody implant adaptable to allow placement of a potentially larger implant through a smaller opening in a patient's body, including, but not limited to, placement into a surgically-corrected disc space between two adjacent vertebrae of a spine.

It is another object of the present invention to provide an expandable interbody implant which can, in one embodiment, be inserted at an oblique angle with respect to an axis defined between an anterior surface and a posterior surface of a disc space, and in other embodiments, also be inserted along the axis from the anterior surface or the posterior surface.

It is a further object of the present invention to provide an expandable interbody implant having an improved driving link, enabling a surgeon to smoothly and reliably expand the implant to a selected height.

It is a further object of the present invention to provide an expandable interbody implant that maintains a near-constant graft volume chamber to avoid formation of pockets in the bone graft as the implant expands.

It is a further object of the present invention to provide an expandable interbody implant with improved control over loss, during expansion, of bone graft material stored within the implant.

These and other objects of the present invention will be apparent from review of the following specification and the accompanying drawings.

In view of the above objects, an expandable interbody implant, in accordance with the present invention, includes a leading end, and a trailing end, adapted for insertion at least into a disc space having a surgically-corrected height, between two adjacent vertebrae of a spine.

An upper member has an upper surface extending between the leading end and the trailing end, and an upper opening defined in the upper surface.

A lower member has a lower surface extending between the leading end and the trailing end, pivotally connected to the upper member at least via a drive link, and a lower opening defined in the lower surface.

A bone graft storage portion is provided intermediate the leading end and the trailing end, including a hollow portion configured to be packed with a selected volume of bone growth material and adapted to allow bone growth between the adjacent vertebrae via the upper and lower openings and the bone graft storage portion. A translational wall is movably mounted between the bone graft storage portion and the trailing end.

An actuator opening is defined proximate the trailing end, and configured for insertion therein of an actuator.

The actuator, following insertion thereof into the actuator opening, pushes the bone graft storage portion toward the leading end and into engagement with the drive link, thereby pushing the drive link forward and moving the upper member upward away from the lower member.

The drive link includes an elongated member having opposing first and second ends, the first end being pivotally attached to the upper member proximate the leading end, and the second end being movably mounted on the lower member proximate the bone graft storage portion, and a ramp portion having a surface defined between the first end and the second end.

The bone graft storage portion, when being pushed forward by the actuator, is adapted to engage the second end of the drive link, pushing it along the lower member, thereby resulting in pivotable translation between the first end of the drive link and the upper member.

The pivotable translation between the first end of the drive member and the upper member continues until the surface of the ramp portion engages the front end of the bone graft storage portion.

The translational wall is mounted in a track at a rear portion of the hollow portion. Pivoting the upper member upward engages the translational wall, thereby raising it upward in the track. An upper surface of the translational wall is adapted to remain substantially flush with an inner surface of the upper member, thereby assisting in preventing loss of the bone graft material from the hollow portion of the bone graft storage portion.

The surface of the ramp of the drive link comes into contact with a front end of the bone graft storage portion, thereby preventing formation of pockets in the bone graft material and keeping the volume of the bone graft material substantially constant.

DETAILED DESCRIPTION OF THE PREFERRED EMBODIMENTS

Figure 1:
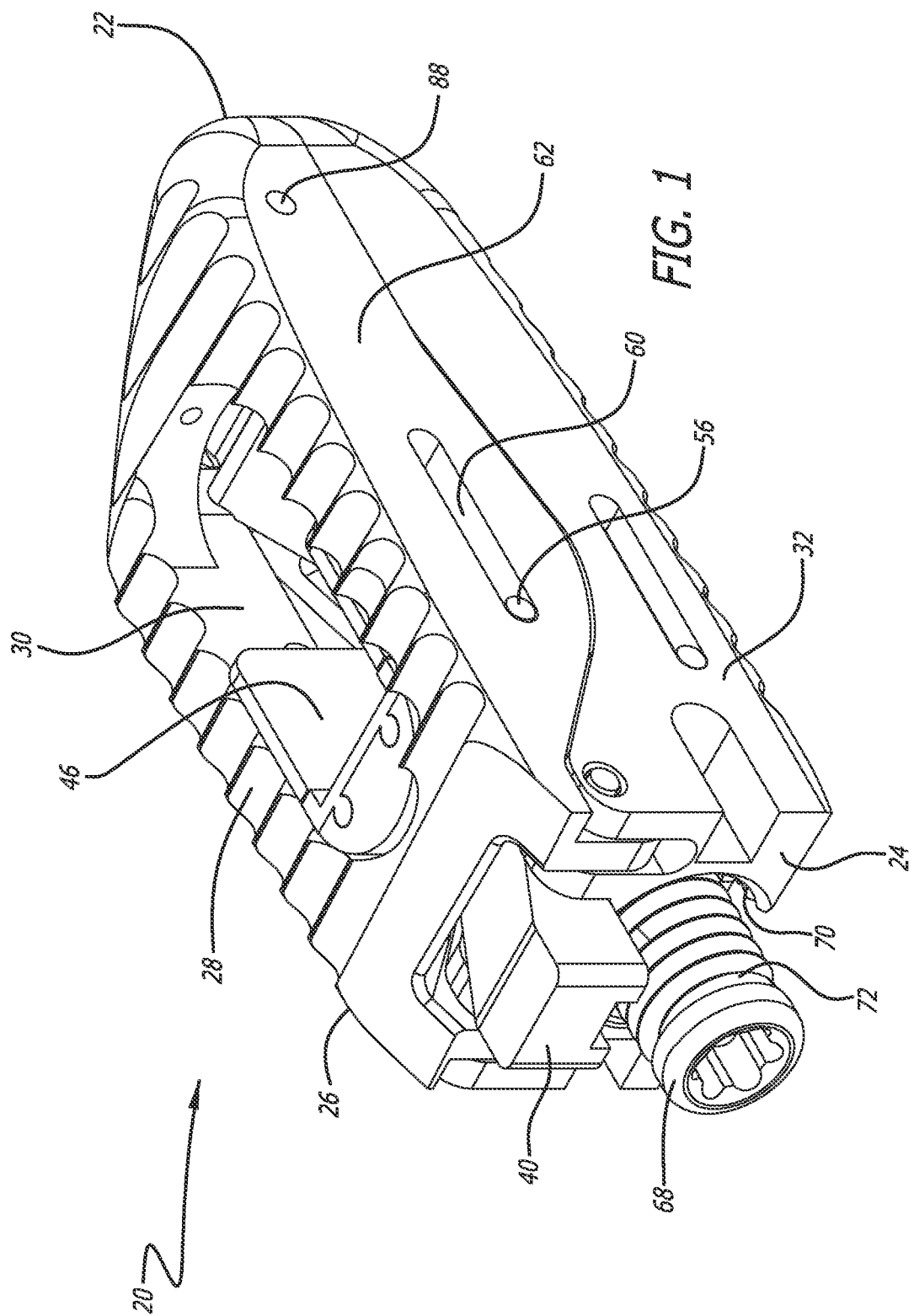
FIG. 1 is a trailing end perspective view of an expandable interbody implant in accordance with an embodiment of the present invention.

Other embodiments of the invention will be apparent to those skilled in the art from consideration of the specification and practice of the invention disclosed herein. It is intended that the embodiments described below be considered as exemplary only, with a true scope and spirit of the invention being indicated by the appended claims.

As shown in FIGS. 1-7, an expandable interbody implant 20 includes a leading end 22 and a trailing end 24. Implant 20 is adapted for insertion at least into a disc space having a surgically-corrected height between two adjacent vertebrae of a spine. Implant 20, moreover, is adapted for movement from an unexpanded position to an expanded position.

Implant 20 includes an upper member 26, having an upper surface 28 extending between leading end 22 and trailing end 24, with an upper opening 30 defined in upper surface 28.

Implant 20 further includes a lower member 32, having a lower surface 34 extending between leading end 22 and trailing end 24, with a lower opening 36 defined in lower surface 34.

Figure 2:
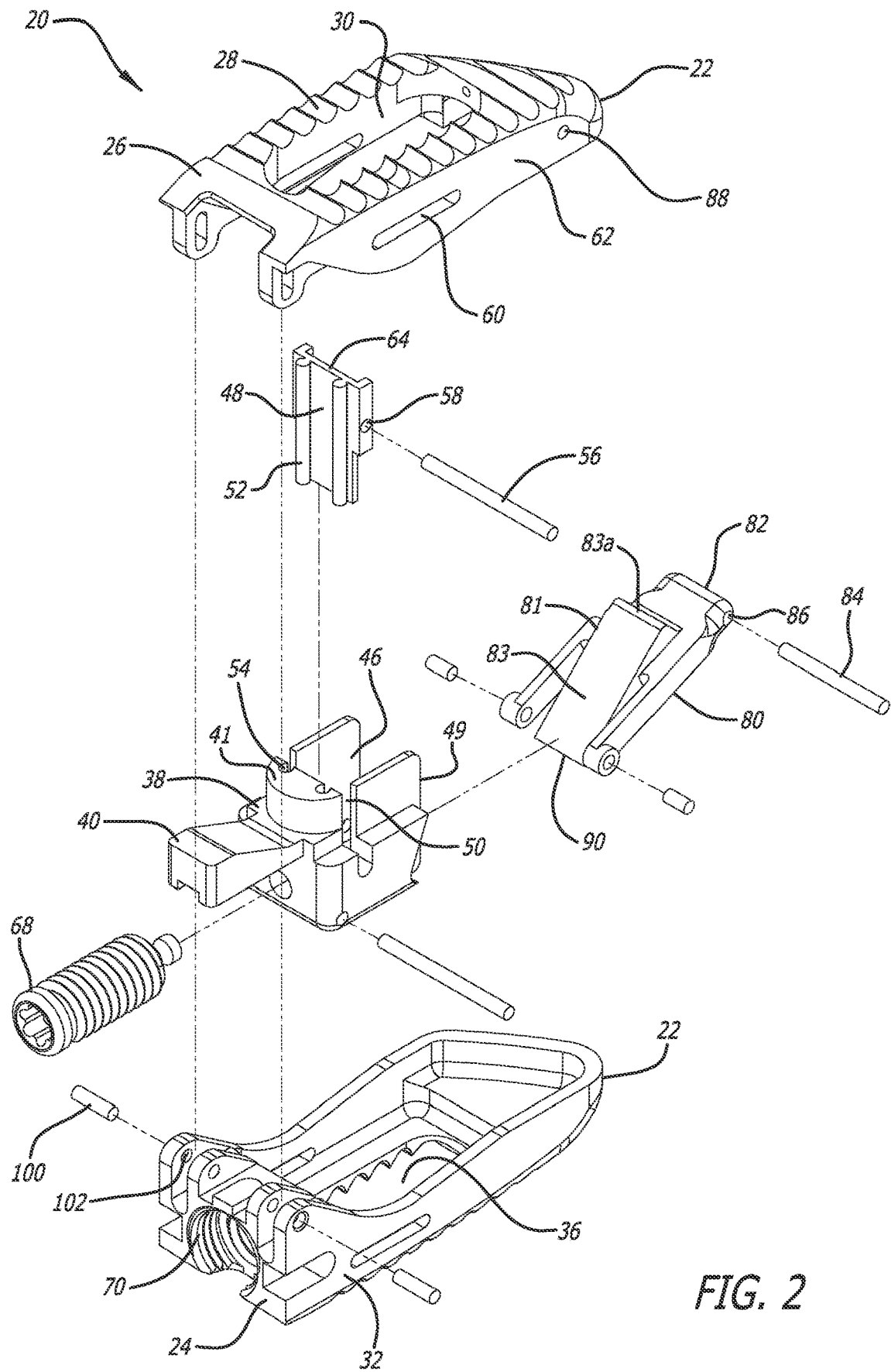
FIG. 2 is an exploded perspective view of an expandable interbody implant in accordance with the present invention.
Figure 5:
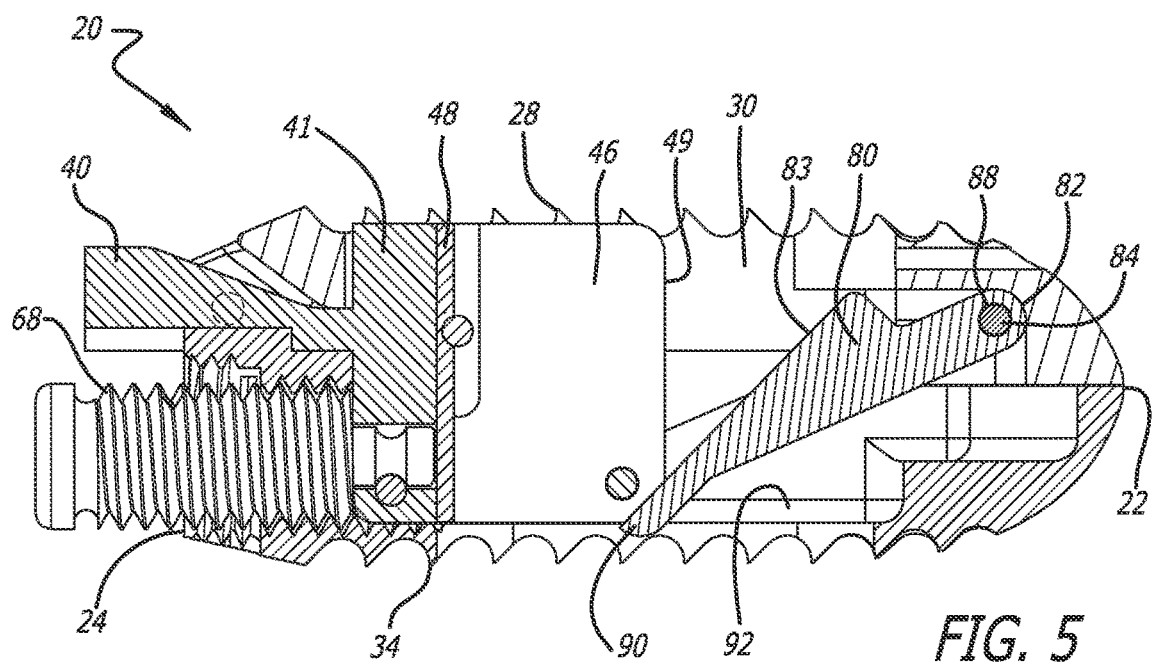
FIG. 5 is a cross-sectional side view of an expandable interbody implant in accordance with the present invention, in an unexpanded position.
Figure 6:
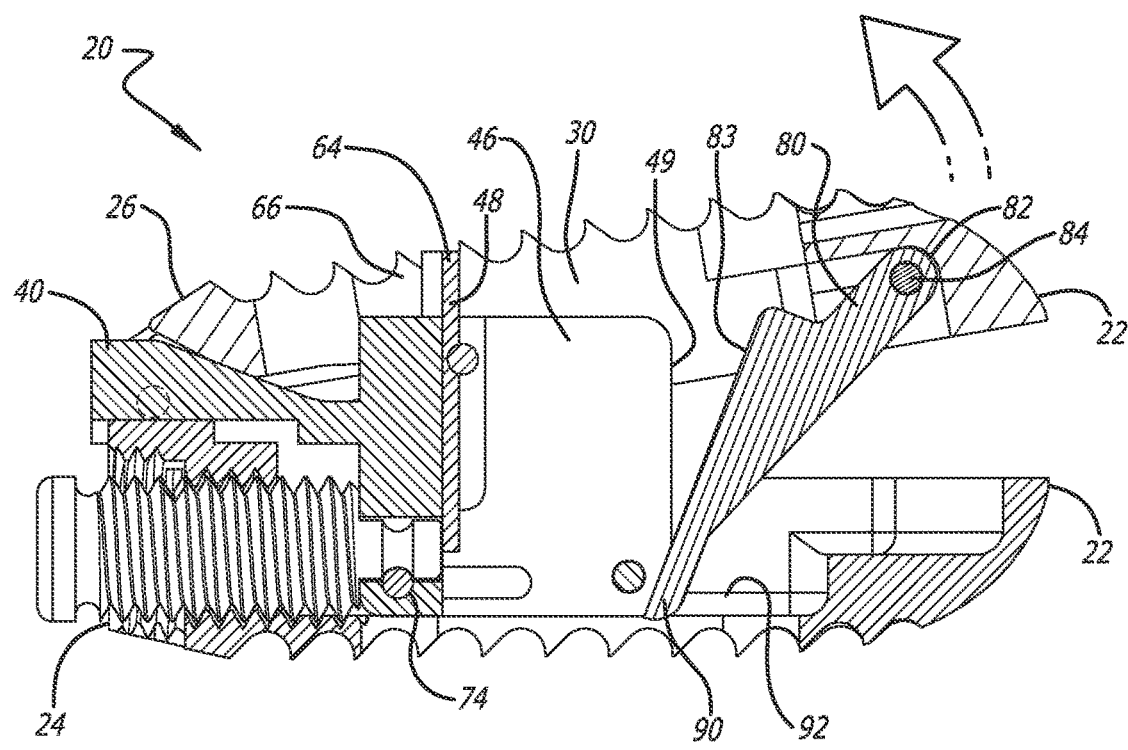
FIG. 6 is a cross-sectional side view of an expandable interbody implant in accordance with the present invention, in a partially-expanded position.

A bone graft storage portion 38 is preferably provided intermediate leading end 22 and trailing end 24. As shown in FIGS. 2 and 5-6, the bone graft storage portion 38 includes a rearward-extending portion 40, a rear end portion 41, and a hollow portion 46 sized to receive a selected volume of bone graft material, which may be of a type well-known in the art. As shown in FIG. 2, the side walls of hollow portion 46 align with rear portions of the sides of the upper and lower openings 30 and 36. Once implant 20 is implanted in the disc space, the bone graft material is adapted to facilitate bone growth between the adjacent vertebrae, via upper opening 30, hollow portion 46, and lower opening 36. In a preferred embodiment, as shown in FIGS. 2-6, end portion 41 has a generally hemi-cylindrical configuration generally corresponding in shape to a portion of the perimeter of upper opening 30.

In a preferred embodiment, and as shown in FIGS. 2-6, a translational wall 48 is movably provided in a slot 50 provided in bucket portion 38 between rear end portion 41 and hollow portion 46. Preferably, translational wall 48 includes a pair of vertical extensions 52, slidably mounted in a pair of tracks 54 defined in end portion 41. As shown in FIG. 2, vertical extensions 52 and tracks 54 have a cylindrical configuration, but any configuration, e.g., a rectangular configuration, is within the scope of the invention. In addition, a pin 56 extends through an aperture 58 in the translational wall 48. As shown in FIGS. 1-3, and 7, pin 56 inserts through an oval-shaped aperture 60 defined in a side wall 62 of upper member 26. Pin 56 is adapted to slide in the oval-shaped aperture 60.

An actuator 68 is adapted to be inserted into and move through an actuator opening 70 in trailing end 24 of implant 20. Preferably, actuator 68 is a threaded actuator having a threaded portion 72 and an actuating end 74. The threads defined on threaded portion 72 are configured to threadably engage corresponding threads in actuator opening 70. A threaded actuator and threaded opening are preferred because, once implant 20 is expanded, the threaded engagement between actuator 68 and actuator opening 70 assists in retaining implant 20 in its expanded position. The invention, however, is not limited to use with a threaded actuator or threaded actuator opening. Other actuator configurations, and corresponding actuator opening configurations, which are well-known in the art can be used, and are within the scope of the invention.

The implant includes a drive link 80. Drive link 80 preferably is configured as an elongated member having a first end 82, and an opposed second end 90, and a ramp portion 81 intermediate the two opposing end portions, ramp portion 81 including a face portion 83 terminating in a peak portion 83a. As shown in FIGS. 2 and 5-6, first end 82 includes an elongated pin 84 extending through an aperture 86 in the first end, and also through an aperture 88 defined in side wall 62 of upper member 26, proximate leading end 22. As further shown in FIGS. 2 and 5-6, second end 90 is movably mounted on an inner surface 92 of lower member 32.

Figure 7:
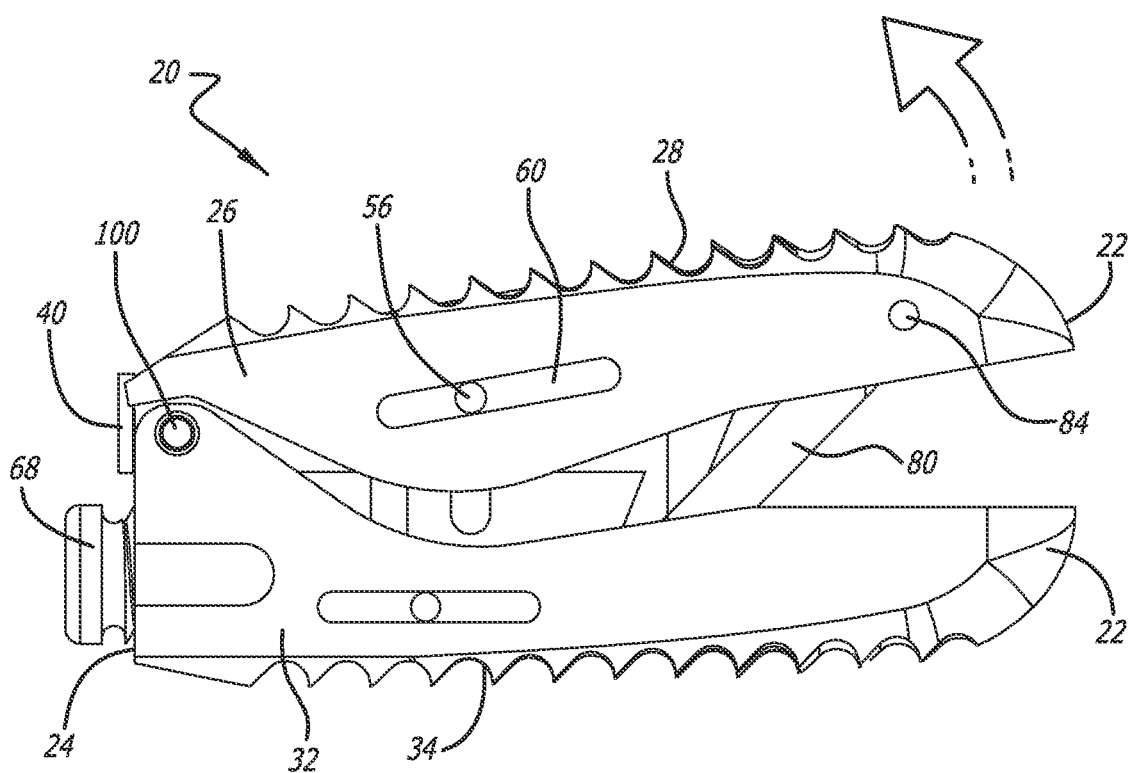
FIG. 7 is a side view of an expandable interbody implant in accordance with the present invention, in the partially-expanded position.

Insertion and placement of a preferred embodiment of the expandable interbody implant in accordance with the present invention will be explained below:

As shown in FIGS. 5-7, forward movement of actuator 68 brings actuating end 74 into contact with rear end portion 41 of bucket portion 38. Bucket portion 38, including hollow portion 46 is pushed forward until the front of hollow portion 46 engages second end 90 of drive link 80. Second end 90 of drive link 80 is pushed forward on inner surface 92 of lower member 32, causing first end 82 and ramp portion 81 of drive link 80 to pivot upward. The upward movement of first end 82 pushes upper member 26 upward, in an upward pivotal motion, up and away from lower member 32, pivoting on a pair of pins 100, inserted through apertures 102, which join upper and lower members 26 and 32 together proximate trailing end 24.

As upper member 26 moves upward, pin 56 slides in oval-shaped aperture 60, thereby raising translational wall 48 upward, as shown in FIG. 6. As shown in FIGS. 5-6, as a result of this configuration, an upper surface 64 of translational wall 48, which is substantially flush with an inner surface 66 of upper member 26 when implant 20 is in the unexpanded position, continues to remain substantially flush with inner surface 66 of upper member 26, throughout the upward pivotal movement of upper member 26. As further shown in FIG. 6, the upward movement of upper wall 48 corresponding to the pivotal upward movement of upper member 26 raises translational wall 48 to a position where it substantially prevents any of the selected volume of bone graft material packed into a bone graft storage portion 46 from escaping out of the bone graft storage space in the direction of translational wall 48 during expansion of the implant, thereby helping to retain the selected volume of bone graft material within implant 20.

Pivotal upward expansion of upper member 26 is limited by face portion 83 of the ramp portion 81 of drive link 80. Face 83 eventually comes into contact with a front surface 49 of the bucket portion 38, thereby acting as a stop, and preventing further pivotal expansion of the implant 20.

Moreover, as the bone graft storage portion 38 moves forward to actuate the implant, the graft volume defined by the bone graft storage portion on the face portion 83 on the "front end," and the upper and lower endplates of the adjacent vertebral bodies (via the upper and lower openings 30 and 36 respectively), remains substantially constant because, as the top-to-bottom dimension of the implant increases with expansion, the front-to-back dimension of the hollow portion 46 between the translational wall 48 and the face 83 in contact with the front surface 49 decreases simultaneously, thereby reducing formation of pockets in the bone graft material stored in the bone graft storage portion 38.

Leading end 22 of implant 20 can have different configurations.

In one preferred embodiment, as shown in FIGS. 1-2, leading end 22 has a substantially rounded, bullet-shaped configuration.

Figure 3:
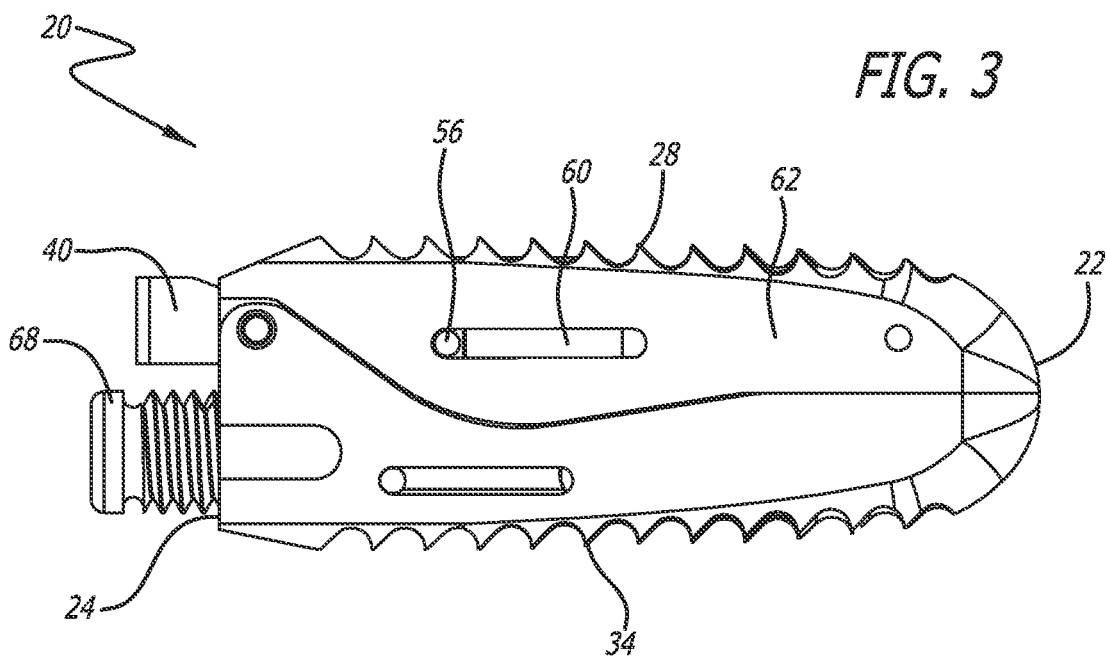
FIG. 3 is a side elevational view of one embodiment of an expandable interbody implant in accordance with the present invention, adapted for oblique, anterior, or posterior insertion and placement in a disc space.
Figure 4:
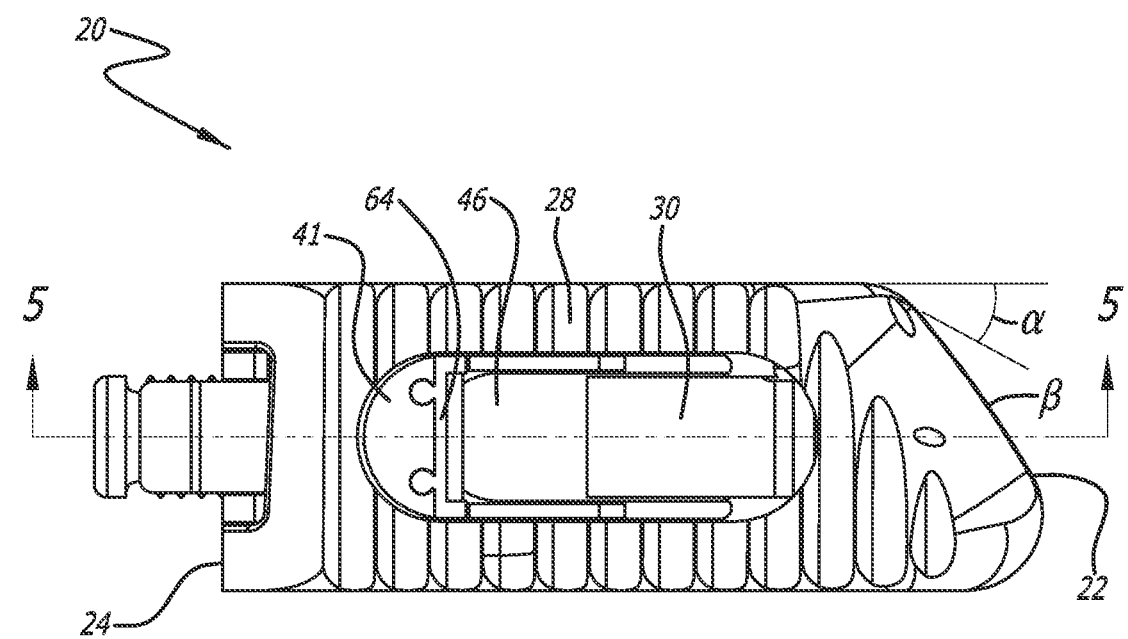
FIG. 4 is a top view of the embodiment of FIG. 3.
Figure 9:
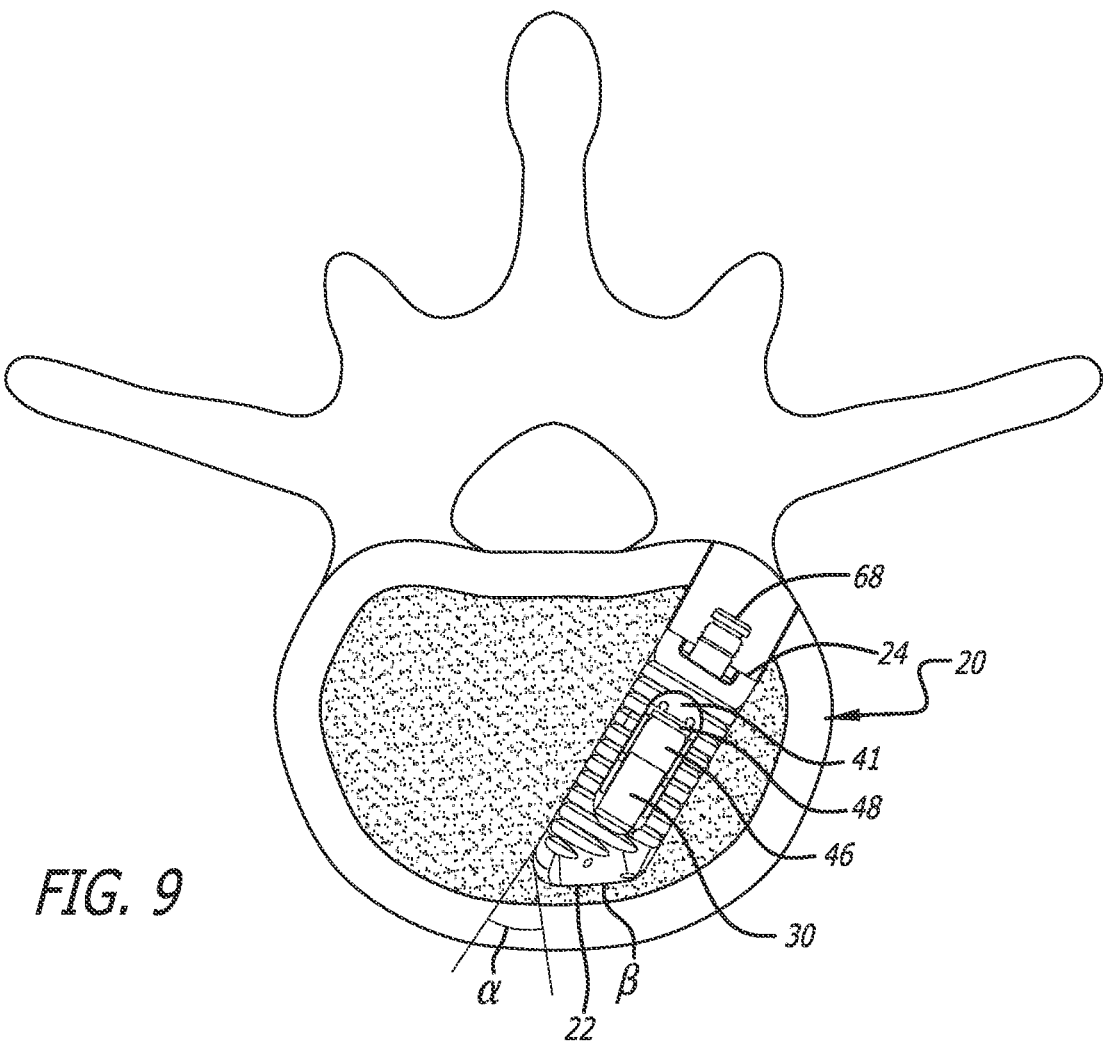
FIG. 9 is a top view of an expandable interbody implant in accordance with the present invention, having a beveled leading end, inserted into a surgically-corrected disc space between two adjacent vertebrae of a spine, at an oblique angle with respect to an axis extending from an anterior portion of the disc space to a posterior portion of the disc space.

In another preferred embodiment, as shown in FIGS. 3-4, and 9, leading end 22 has a beveled surface β defining an oblique angle α between upper surface 28 and lower surface 34. Oblique angle α preferably is approximately 45°. As shown in FIG. 9, beveled leading end 22 of this embodiment is capable of insertion into the disc space at an oblique angle, preferably 45°, with respect to the axis defined between anterior and posterior portions of the disc space. The beveled leading end of this embodiment also is capable of insertion into the disc space along the axis defined between anterior and posterior portions of the disc.

Figure 8:
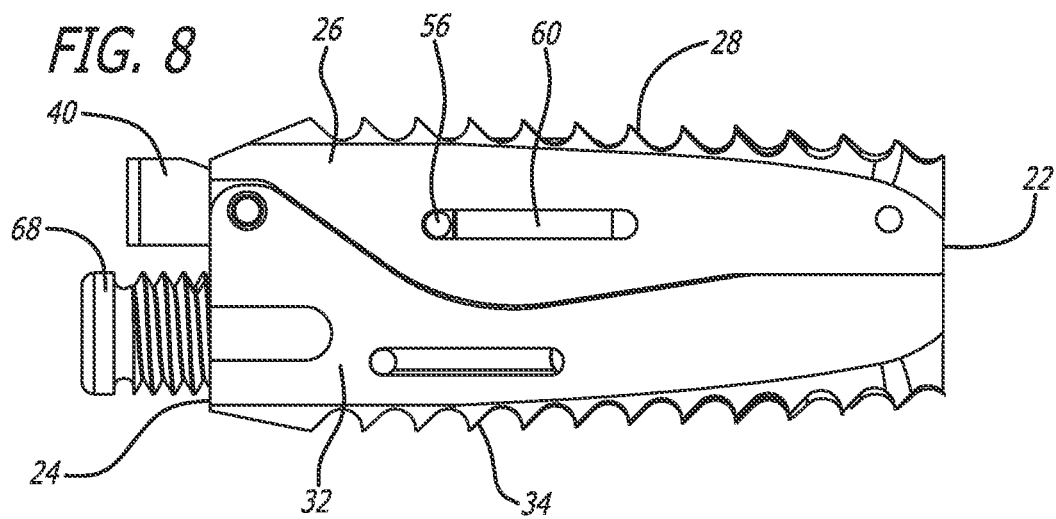
FIG. 8 is a side elevational view of another embodiment of an expandable interbody implant in accordance with the present invention.
Figure 10:
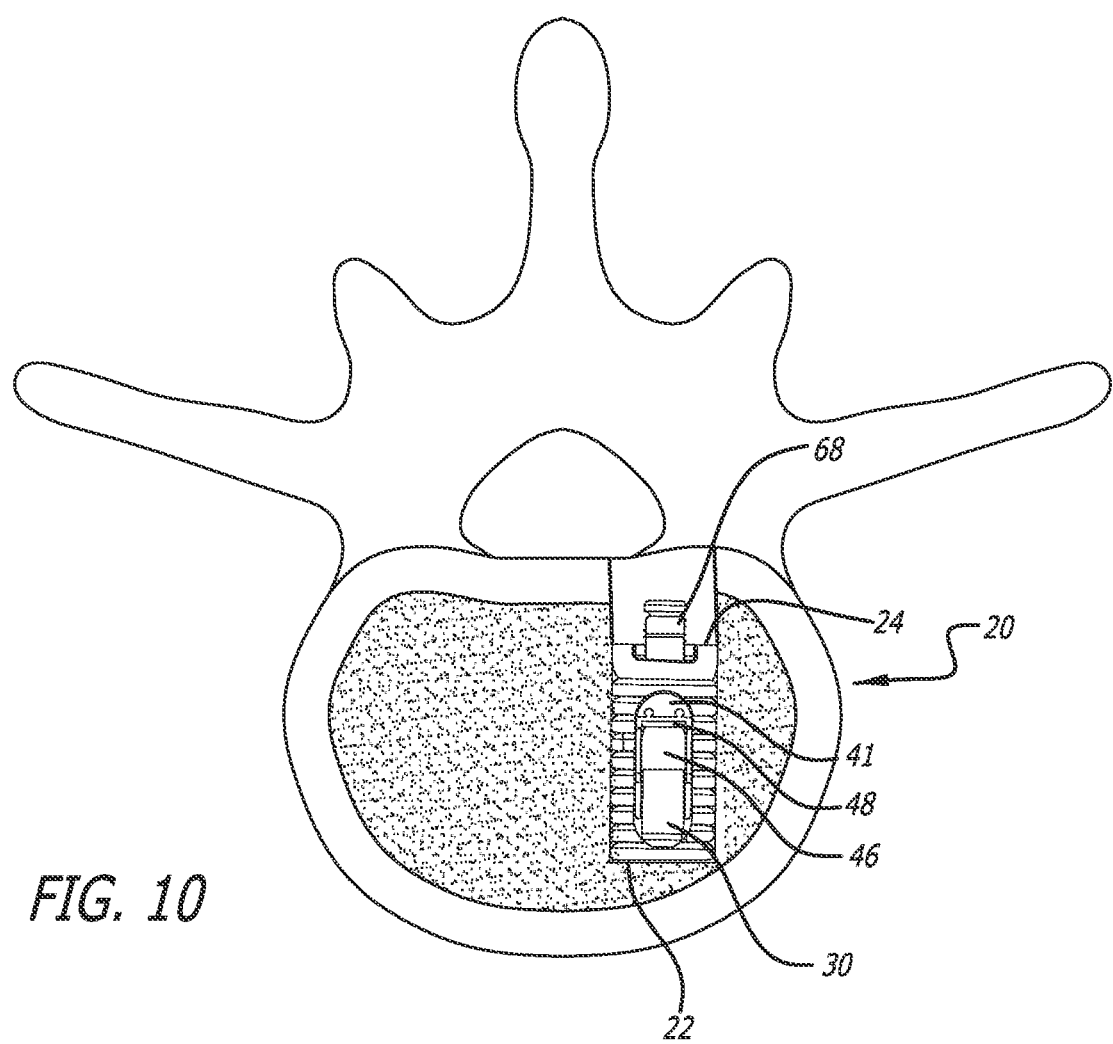
FIG. 10 is a top view of an expandable interbody implant in accordance with the invention, having a substantially vertical planar leading end, inserted into a surgically-corrected disc space between two adjacent vertebrae of a spine, along an axis extending from a posterior portion of the disc space to an anterior portion of the disc space.

In another embodiment, as shown in FIG. 8, leading end 22 has a generally planar shape, defining substantial right angles with respect to each of upper and lower surfaces 28 and 34, respectively. As shown in FIG. 10, leading end 22 of this embodiment also is configured for insertion of the implant into the disc space at least along the axis defined between anterior and posterior portions of the disc space.

There is disclosed in the above description and the drawings, implants, which fully and effectively accomplish the objectives of this invention. It will be apparent, however, that variations and modifications of the disclosed embodiments may be made without departing from the principles of the invention or the scope of the appended claims.

What is claimed is:

1. An expandable interbody spinal implant comprising:
a proximal end and an opposite distal end;
an upper member having an upper surface extending between the proximal end and the distal end;
a lower member having a lower surface extending between the proximal end and the distal end, the lower member being pivotally connected to the upper member;
a bone graft storage portion provided intermediate the proximal end and the distal end, the bone graft storage portion including a proximal wall and a hollow cavity adjacent the proximal wall, the hollow cavity being configured to be packed with a selected volume of bone growth material, the bone graft storage portion being non-rotatable and capable of being moved forward from a first position to a second position with the first position being closer to the proximal end than the second position, and the bone graft storage portion having at least one slot portion adjacent the proximal wall;
a translational wall movably received in the at least one slot portion formed in the bone graft storage portion, the translational wall being moveable between a lower first position and an upper second position via movement in the at least one slot portion;
a drive link pivotally connected to the upper member, and being slidably mounted relative to the lower member and capable of being moved forward toward the distal end by the bone graft storage portion; and
an actuator opening and an actuator, the actuator opening being positioned proximate the proximal end and being configured for insertion of the actuator therein, the actuator being configured to move the bone graft storage portion between the first position and the second position;
wherein movement of the actuator in the actuator opening moves the bone graft storage portion from the first position to the second position, and correspondingly moves at least a portion of the drive link forward toward the distal end to pivot a portion of the upper member upwardly relative to the lower member; and
wherein pivotal movement of the portion of the upper member moves the translational wall upwardly from the lower first position to the upper second position in the at least one slot portion.

2. The implant of claim 1, wherein the drive link includes a first end and an opposite second end, the first end of the drive link being closer to the proximal end of the implant than the second end of the drive link, and the forward movement of the drive link pivots the second end of the drive link upward.

3. The implant of claim 2, wherein the first end of the drive link is pivotally attached to the bone graft storage portion.

4. The implant of claim 2, wherein the drive link includes a surface positioned between the first end and the second end thereof, and pivotal of the drive link moves the surface toward the hollow portion of bone graft storage to assist in preventing loss of the bone growth material from the hollow portion of the bone graft storage portion.

5. The implant of claim 1, wherein the translational wall is moveably attached to the upper member via a pin inserted through the translational wall and received in at least one aperture formed in the upper member.

6. The implant of claim 1, wherein rotation of the actuator in the actuator opening is translated into forward movement of the bone graft storage portion.

7. The implant of claim 1, wherein the upper member and the lower member are pivotally attached to one another adjacent the proximal end of the implant.

8. The implant of claim 7, wherein the upper member includes an angled lower surface, and the bone graft storage portion includes an angled upper surface, and contact of the angled lower surface and the angled upper surface during movement of the bone graft storage portion from the first position to the second position aids in pivoting the portion of the upper member relative to the lower member.

9. An expandable interbody spinal implant comprising:
a proximal end and an opposite distal end;
an upper member;
a lower member;
a bone graft storage portion provided intermediate the proximal end and the distal end, the bone graft storage portion including a proximal wall and a hollow cavity adjacent the proximal wall, the bone graft storage portion being non-rotatable and capable of being moved between the proximal end and the distal end, and the bone graft storage portion having at least one slot portion formed therein;
a translational wall movably received in the at least one slot portion formed in the bone graft storage portion, the translational wall being moveable between a lower first position and an upper second position via movement in the at least one slot portion;
a drive link pivotally connected to the upper member, and being slidably mounted relative to the lower member and capable of being moved forward toward the distal end by the bone graft storage portion; and
an actuator opening and an actuator, the actuator opening being positioned proximate the proximal end and being configured for insertion of the actuator therein, the actuator being configured to move the bone graft storage portion between the first position and the second position;
wherein movement of the actuator in the actuator opening moves the bone graft storage portion forward from the first position to the second position, and correspondingly moves at least a portion of the drive link forward toward the distal end to pivot a portion of the upper member upwardly relative to the lower member; and
wherein pivotal movement of the portion of the upper member moves the translational wall upwardly from the lower first position to the upper second position in the at least one slot portion.

10. The implant of claim 9, wherein the drive link includes a first end and an opposite second end, the first end of the drive link being closer to the proximal end of the implant than the second end of the drive link, and the forward movement of the drive link pivots the second end of the drive link upward.

11. The implant of claim 10, wherein the first end of the drive link is pivotally attached to the bone graft storage portion.

12. The implant of claim 10, wherein the drive link includes a surface positioned between the first end and the second end thereof, and pivotal movement of the drive link moves the surface toward the hollow portion of bone graft storage to assist in preventing loss of the bone growth material from the hollow portion of the bone graft storage portion.

13. The implant of claim 9, wherein the translational wall is moveably attached to the upper member via a pin inserted through the translational wall and received in at least one aperture formed in the upper member.

14. The implant of claim 9, wherein rotation of the actuator in the actuator opening is translated into forward movement of the bone graft storage portion.

15. The implant of claim 9, wherein the upper member and the lower member are pivotally attached to one another adjacent the proximal end of the implant.

16. The implant of claim 15, wherein the upper member includes an angled lower surface, and the bone graft storage portion includes an angled upper surface, and contact of the angled lower surface and the angled upper surface during movement of the bone graft storage portion from the first position to the second position aids in pivoting the portion of the upper member relative to the lower member.

17. An expandable interbody spinal implant comprising:
a proximal end and an opposite distal end;
an upper member;
a lower member;
a bone graft storage portion provided intermediate the proximal end and the distal end, the bone graft storage portion including a proximal wall and a hollow cavity adjacent the proximal wall, the bone graft storage portion being non-rotatable and capable of being moved forward from a first position to a second position with the first position being closer to the proximal end than the second position, and the bone graft storage portion having at least one slot portion formed therein;
a translational wall movably received in the at least one slot portion formed in the bone graft storage portion, the translational wall being moveable between a lower first position and an upper second position via movement in the at least one slot portion;
a drive link having a first end and an opposite second end, the drive link being pivotally connected to the bone graft storage portion adjacent first end thereof, being pivotally connected to the upper member adjacent the second end thereof, and being slidably mounted relative to the lower member, the drive link being capable of being moved forward toward the distal end by the bone graft storage portion, and the second end of the drive link being capable of pivoting upward during forward movement of the drive link toward the distal end; and
an actuator opening and an actuator, the actuator opening being positioned proximate the proximal end and being configured for insertion of the actuator therein, the actuator being being configured to move the bone graft storage portion between the first position and the second position;
wherein movement of the actuator in the actuator opening moves the bone graft storage portion from the first position to the second position, and correspondingly moves at least a portion of the drive link forward toward the distal end to pivot a portion of the upper member upwardly relative to the lower member; and
wherein pivotal movement of the portion of the upper member moves the translational wall upwardly from the lower first position to the upper second position in the at least one slot portion.

18. The implant of claim 17, wherein the drive link includes a surface positioned between the first end and the second end thereof, and pivotal movement of the drive link moves the surface toward the hollow portion of bone graft storage to assist in preventing loss of the bone growth material from the hollow portion of the bone graft storage portion.

19. The implant of claim 17, wherein the translational wall is moveably attached to the upper member via a pin inserted through the translational wall and received in at least one aperture formed in the upper member.

20. The implant of claim 17, wherein rotation of the actuator in the actuator opening is translated into forward movement of the bone graft storage portion.

\* \* \* \* \*